United States Patent
Jakel et al.

(10) Patent No.: US 10,119,157 B2
(45) Date of Patent: Nov. 6, 2018

(54) SYSTEMS AND METHODS FOR PRODUCING A SUGAR STREAM

(71) Applicant: Fluid Quip Process Technologies, LLC, Springfield, OH (US)

(72) Inventors: Neal Jakel, Cedar Rapids, IA (US); John Kwik, Bellbrook, OH (US); Michael Franko, Denver, CO (US); Andrew Whalen, Cincinnati, OH (US)

(73) Assignee: Fluid Quip Process Technologies, LLC, Springfield, OH (US)

(*) Notice: Subject to any disclaimer, the term of this patent is extended or adjusted under 35 U.S.C. 154(b) by 0 days.

(21) Appl. No.: 15/230,280

(22) Filed: Aug. 5, 2016

(65) Prior Publication Data

US 2017/0022466 A1    Jan. 26, 2017

Related U.S. Application Data

(62) Division of application No. 15/074,417, filed on Mar. 18, 2016, now Pat. No. 9,777,303.

(60) Provisional application No. 62/196,108, filed on Jul. 23, 2015.

(51) Int. Cl.

| | |
|---|---|
| C12M 1/00 | (2006.01) |
| C12P 19/02 | (2006.01) |
| C12P 19/14 | (2006.01) |
| C13K 1/06 | (2006.01) |
| C12P 7/06 | (2006.01) |
| C12M 1/33 | (2006.01) |
| C12P 7/10 | (2006.01) |
| C12P 7/64 | (2006.01) |

(52) U.S. Cl.
CPC ............. *C12P 19/02* (2013.01); *C12M 21/12* (2013.01); *C12M 23/58* (2013.01); *C12M 29/04* (2013.01); *C12M 45/02* (2013.01); *C12M 45/09* (2013.01); *C12M 47/10* (2013.01); *C12P 7/06* (2013.01); *C12P 7/10* (2013.01); *C12P 7/649* (2013.01); *C12P 19/14* (2013.01); *C13K 1/06* (2013.01); *C12P 2203/00* (2013.01); *Y02E 50/13* (2013.01); *Y02E 50/16* (2013.01); *Y02E 50/17* (2013.01); *Y02E 50/343* (2013.01)

(58) Field of Classification Search
None
See application file for complete search history.

(56) References Cited

U.S. PATENT DOCUMENTS

| | | |
|---|---|---|
| 4,330,625 A | 5/1982 | Miller et al. |
| 4,361,651 A | 11/1982 | Keim |
| 4,407,955 A | 10/1983 | Muller et al. |
| 4,578,353 A | 3/1986 | Assarsson et al. |
| 6,962,722 B2 | 11/2005 | Dawley et al. |
| 7,452,425 B1 | 11/2008 | Langhauser |
| 7,488,390 B2 | 2/2009 | Langhauser |
| 7,494,675 B2 | 2/2009 | Abbas et al. |
| 7,985,847 B2 | 7/2011 | Belanger et al. |
| 8,278,080 B2 | 10/2012 | Yoon |
| 8,557,540 B2 | 10/2013 | Burlew et al. |
| 8,652,818 B2 | 2/2014 | Lawton, Jr. et al. |
| 8,722,372 B2 | 5/2014 | Kiuchi et al. |
| 8,778,433 B2 | 7/2014 | Lee |
| 9,012,191 B2 | 4/2015 | Lee |
| 9,068,205 B2 | 6/2015 | Purtle et al. |
| 9,273,329 B2 | 3/2016 | Kusuda et al. |
| 9,523,104 B2 | 12/2016 | Fuchs et al. |
| 9,909,158 B2 | 3/2018 | Yamada et al. |
| 9,920,346 B2 | 3/2018 | Funada et al. |
| 9,926,613 B2 | 3/2018 | Kishimoto et al. |
| 2006/0083823 A1 | 4/2006 | Fox et al. |
| 2006/0251762 A1 | 11/2006 | Jansen et al. |
| 2007/0014905 A1 | 1/2007 | Chen et al. |
| 2007/0020375 A1 | 1/2007 | Jansen et al. |
| 2008/0260902 A1 | 10/2008 | Van Houten et al. |
| 2009/0238918 A1 | 9/2009 | Jansen et al. |
| 2009/0258106 A1 | 10/2009 | Jansen et al. |
| 2011/0236946 A1 | 9/2011 | Maclachlan et al. |
| 2012/0244590 A1 | 9/2012 | Lee |

(Continued)

FOREIGN PATENT DOCUMENTS

WO    2014182807 A1    11/2014

OTHER PUBLICATIONS

European Patent Office, Search Report issued in European Patent Application No. 16179909.3 dated Dec. 15, 2016, 10 pages.

(Continued)

*Primary Examiner* — Robert J Yamasaki

(74) *Attorney, Agent, or Firm* — Wood Herron & Evans LLP

(57) ABSTRACT

An improved dry grind system and method for producing a sugar stream from grains or similar carbohydrate sources and/or residues, such as for biofuel production. In particular, a sugar/carbohydrate stream, which includes a desired Dextrose Equivalent (DE) where DE describes the degree of conversion of starch to dextrose (aka glucose) and/or has had removed therefrom an undesirable amount of unfermentable components, can be produced after saccharification and prior to fermentation (or other sugar conversion process), with such sugar stream being available for biofuel production, e.g., alcohol production, or other processes. In addition, the systems and methods also can involve the removal of certain grain components, e.g., corn kernel components, including protein, oil and/or fiber, prior to fermentation or other conversion systems. In other words, sugar stream production and/or grain component separation occurs on the front end of the system and method.

24 Claims, 5 Drawing Sheets

(56) References Cited

U.S. PATENT DOCUMENTS

| | | |
|---|---|---|
| 2013/0065289 A1 | 3/2013 | Carlson |
| 2013/0236936 A1 | 9/2013 | Lee |
| 2013/0295661 A1 | 11/2013 | Roesch et al. |
| 2014/0024064 A1 | 1/2014 | Burlew et al. |
| 2014/0193872 A1 | 7/2014 | Chen et al. |
| 2014/0227757 A1 | 8/2014 | Jin et al. |
| 2014/0234935 A1 | 8/2014 | Kusuda et al. |
| 2014/0287469 A1 | 9/2014 | Medoff et al. |
| 2014/0356915 A1 | 12/2014 | Retsina et al. |
| 2015/0004647 A1 | 1/2015 | Niwa et al. |
| 2015/0344921 A1 | 12/2015 | Kacmar et al. |
| 2016/0160242 A1 | 6/2016 | Mimitsuka et al. |
| 2016/0186215 A1 | 6/2016 | Redford |
| 2016/0289704 A1 | 10/2016 | Medoff |
| 2016/0289705 A1 | 10/2016 | Medoff |
| 2016/0289706 A1 | 10/2016 | Medoff |
| 2016/0298141 A1 | 10/2016 | Medoff |
| 2016/0298142 A1 | 10/2016 | Yu et al. |
| 2016/0312258 A1 | 10/2016 | Ikeo et al. |

OTHER PUBLICATIONS

United States Patent Office, Office Action issued in U.S. Appl. No. 15/074,417 dated Nov. 4, 2016, 17 pages.
United States Patent Office, Notice of Allowance issued in U.S. Appl. No. 15/074,417 dated Jun. 13, 2017, 9 pages.
European Patent Office, Examimation Report issued in EP 16179909.3 dated Nov. 29, 2017, 10 pages.
European Patent Office, Office Action issued in European Patent Application No. 16179909.3 dated Jul. 6, 2018, 5 pages.

SYSTEMS AND METHODS FOR PRODUCING A SUGAR STREAM

TECHNICAL FIELD

The present invention relates generally to systems and methods for use in the biofuel, biochemical, food, feed, nutrition, and/or pharmacy industries and, more specifically, to improved dry grind systems and methods for producing a sugar stream, such as for biofuel production.

BACKGROUND

The conventional processes for producing various types of biofuels, such as alcohol and other chemicals, from grains generally follow similar procedures. Wet mill processing plants convert, for example, corn grain, into several different co-products, such as germ (for oil extraction), gluten feed (high fiber animal feed), gluten meal (high protein animal feed) and starch-based products such as alcohol (e.g., ethanol or butanol), high fructose corn syrup, or food and industrial starch. Dry grind plants generally convert grains, such as corn, into two products, namely alcohol (e.g., ethanol or butanol) and distiller's grains with solubles. If sold as wet animal feed, distiller's wet grains with solubles are referred to as DWGS. If dried for animal feed, distiller's dried grains with solubles are referred to as DDGS. This co-product provides a secondary revenue stream that offsets a portion of the overall alcohol production cost.

With respect to the wet mill process, FIG. 1 is a flow diagram of a typical wet mill alcohol (e.g., ethanol) production process 10. The process 10 begins with a steeping step 12 in which grain (e.g., corn) is soaked for 24 to 48 hours in a solution of water and sulfur dioxide in order to soften the kernels for grinding, leach soluble components into the steep water and loosen the protein matrix with the endosperm. Corn kernels contain mainly starch, fiber, protein and oil. The mixture of steeped corn and water is then fed to a degermination mill step (first grinding) 14 in which the corn is ground in a manner that tears open the kernels and releases the germ so as to make a heavy density (8.5 to 9.5 Be) slurry of the ground components, primarily a starch slurry. This is followed by a germ separation step 16 that occurs by flotation and use of a hydrocyclone(s) to separate the germ from the rest of the slurry. The germ is the part of the kernel that contains the oil found in corn. The separated germ stream, which contains some portion of the starch, protein and fiber, goes to germ washing to remove starch and protein, and then to a dryer to produce about 2.7 to 3.2 Lb. (dry basis) of germ per bushel of corn. The dry germ has about 50% oil content on a dry basis.

The remaining slurry, which is now devoid of germ, but containing fiber, gluten (i.e., protein) and starch, is then subjected to a fine grinding step (second grinding) 20 in which there is total disruption of endosperm and release of endosperm components, namely gluten and starch, from the fiber. This is followed by a fiber separation step 22 in which the slurry is passed through a series of screens in order to separate the fiber from starch and gluten and to wash the fiber clean of gluten and starch. The fiber separation stage 22 typically employs static pressure screens or rotating paddles mounted in a cylindrical screen (Paddle Screens). Even after washing, the fiber from a typical wet grind mill contains 15 to 20% starch. This starch is sold with the fiber as animal feed. The remaining slurry, which is now generally devoid of fiber, is subjected to a gluten separation step 24 in which centrifugation or hydrocyclones separate starch from the gluten. The gluten stream goes to a vacuum filter and dryer to produce gluten (protein) meal.

The resulting purified starch co-product then can undergo a jet cooking step 26 to start the process of converting the starch to sugar. Jet cooking refers to a cooking process performed at elevated temperatures and pressures, although the specific temperatures and pressures can vary widely. Typically, jet cooking occurs at a temperature of about 93 to 110° C. (about 200 to 230° F.) and a pressure of about 30 to 50 psi. This is followed by liquefaction 28, saccharification 30, fermentation 32, yeast recycling 34, and distillation/dehydration 36 for a typical wet mill biofuels system. Liquefaction occurs as the mixture or "mash" is held at 90 to 95° C. in order for alpha-amylase to hydrolyze the gelatinized starch into maltodextrins and oligosaccharides (chains of glucose sugar molecules) to produce a liquefied mash or slurry. In the saccharification step 30, the liquefied mash is cooled to about 50° C. and a commercial enzyme known as gluco-amylase is added. The gluco-amylase hydrolyzes the maltodextrins and short-chained oligosaccharides into single glucose sugar molecules to produce a liquefied mash. In the fermentation step 32, a common strain of yeast (*Saccharomyces cerevisae*) is added to metabolize the glucose sugars into ethanol and $CO_2$.

Upon completion, the fermentation mash ("beer") will contain about 15% to 18% ethanol (volume/volume basis), plus soluble and insoluble solids from all the remaining grain components. The solids and some liquid remaining after fermentation go to an evaporation stage where yeast can be recovered as a byproduct. Yeast can optionally be recycled in a yeast recycling step 34. In some instances, the $CO_2$ is recovered and sold as a commodity product. Subsequent to the fermentation step 32 is the distillation and dehydration step 36 in which the beer is pumped into distillation columns where it is boiled to vaporize the ethanol. The ethanol vapor is separated from the water/slurry solution in the distillation columns and alcohol vapor (in this instance, ethanol) exits the top of the distillation columns at about 95% purity (190 proof). The 190 proof ethanol then goes through a molecular sieve dehydration column, which removes the remaining residual water from the ethanol, to yield a final product of essentially 100% ethanol (199.5 proof). This anhydrous ethanol is now ready to be used for motor fuel purposes. Further processing within the distillation system can yield food grade or industrial grade alcohol.

No centrifugation step is necessary at the end of the wet mill ethanol production process 10 as the germ, fiber and gluten have already been removed in the previous separation steps 16, 22, 24. The "stillage" produced after distillation and dehydration 36 in the wet mill process 10 is often referred to as "whole stillage" although it also is technically not the same type of whole stillage produced with a traditional dry grind process described in FIG. 2 below, since no insoluble solids are present. Other wet mill producers may refer to this type of stillage as "thin" stillage.

The wet grind process 10 can produce a high quality starch product for conversion to alcohol, as well as separate streams of germ, fiber and protein, which can be sold as co-products to generate additional revenue streams. However, the overall yields for various co-products can be less than desirable and the wet grind process is complicated and costly, requiring high capital investment as well as high-energy costs for operation.

Because the capital cost of wet grind mills can be so prohibitive, some alcohol plants prefer to use a simpler dry grind process. FIG. 2 is a flow diagram of a typical dry grind alcohol (e.g., ethanol) production process 100. As a general reference point, the dry grind method 100 can be divided into a front end and a back end. The part of the method 100 that occurs prior to distillation 110 is considered the "front end," and the part of the method 100 that occurs after distillation 110 is considered the "back end." To that end, the front end of the dry grind process 100 begins with a grinding step 102 in which dried whole corn kernels can be passed through hammer mills for grinding into meal or a fine powder. The screen openings in the hammer mills or similar devices typically are of a size ⁶⁄₆₄ to ⁹⁄₆₄ inch, or about 2.38 mm to 3.57 mm, but some plants can operate at less than or greater than these screen sizes. The resulting particle distribution yields a very wide spread, bell type curve, which includes particle sizes as small as 45 micron and as large as 2 to 3 mm. The majority of the particles are in the range of 500 to 1200 micron, which is the "peak" of the bell curve.

After the grinding step 102, the ground meal is mixed with cook water to create a slurry at slurry step 103 and a commercial enzyme called alpha-amylase is typically added (not shown). The slurry step 103 is followed by a liquefaction step 104 whereat the pH is adjusted to about 5.2 to 5.8 and the temperature maintained between about 50° C. to 105° C. so as to convert the insoluble starch in the slurry to soluble starch. Various typical liquefaction processes, which occur at this liquefaction step 104, are discussed in more detail further below. The stream after the liquefaction step 104 has about 30% dry solids (DS) content, but can range from about 29-36%, with all the components contained in the corn kernels, including starch/sugars, protein, fiber, starch, germ, grit and oil and salts, for example. Higher solids are achievable, but this requires extensive alpha amylase enzyme to rapidly breakdown the viscosity in the initial liquefaction step. There generally are several types of solids in the liquefaction stream: fiber, germ and grit.

Liquefaction may be followed by separate saccharification and fermentation steps, 106 and 108, respectively, although in most commercial dry grind ethanol processes, saccharification and fermentation can occur simultaneously. This single step is referred to in the industry as "Simultaneous Saccharification and Fermentation" (SSF). Both saccharification and SSF can take as long as about 50 to 60 hours. Fermentation converts the sugar to alcohol. Yeast can optionally be recycled in a yeast recycling step (not shown) either during the fermentation process or at the very end of the fermentation process. Subsequent to the fermentation step 108 is the distillation (and dehydration) step 110, which utilizes a still to recover the alcohol.

Finally, a centrifugation step 112 involves centrifuging the residuals produced with the distillation and dehydration step 110, i.e., "whole stillage" in order to separate the insoluble solids ("wet cake") from the liquid ("thin stillage"). The liquid from the centrifuge contains about 5% to 12% DS. The "wet cake" includes fiber, of which there generally are three types: (1) pericarp, with average particle sizes typically about 1 mm to 3 mm; (2) tricap, with average particle sizes about 500 micron; (3) and fine fiber, with average particle sizes of about 250 micron. There may also be proteins with a particle size of about 45 to 300 micron.

The thin stillage typically enters evaporators in an evaporation step 114 in order to boil or flash away moisture, leaving a thick syrup which contains the soluble (dissolved) solids (mainly protein and starches/sugars) from the fermentation (25 to 40% dry solids) along with residual oil and fine fiber. The concentrated slurry can be sent to a centrifuge to separate the oil from the syrup in an oil recovery step 116. The oil can be sold as a separate high value product. The oil yield is normally about 0.6 lb./bu of corn with high free fatty acids content. This oil yield recovers only about ⅓ of the oil in the corn, with part of the oil passing with the syrup stream and the remainder being lost with the fiber/wet cake stream. About one-half of the oil inside the corn kernel remains inside the germ after the distillation step 110, which cannot be separated in the typical dry grind process using centrifuges. The free fatty acids content, which is created when the oil is heated and exposed to oxygen throughout the front and back-end process, reduces the value of the oil. The (de-oil) centrifuge only removes less than 50% because the protein and oil make an emulsion, which cannot be satisfactorily separated.

The syrup, which has more than 10% oil, can be mixed with the centrifuged wet cake, and the mixture may be sold to beef and dairy feedlots as Distillers Wet Grain with Solubles (DWGS). Alternatively, the wet cake and concentrated syrup mixture may be dried in a drying step 118 and sold as Distillers Dried Grain with Solubles (DDGS) to dairy and beef feedlots. This DDGS has all the corn and yeast protein and about 75% of the oil in the starting corn material. But the value of DDGS is low due to the high percentage of fiber, and in some cases the oil is a hindrance to animal digestion and lactating cow milk quality.

Further with respect to the liquefaction step 104, FIG. 3 is a flow diagram of various typical liquefaction processes that define the liquefaction step 104 in the dry grind process 100. Again, the dry grind process 100 begins with a grinding step 102 in which dried whole corn kernels are passed through hammer mills or similar milling systems such as roller mills, flaking mills, impacted mill or pin mills for grinding into meal or a fine powder. The grinding step 102 is followed by the liquefaction step 104, which itself includes multiple steps as is discussed next.

Each of the various liquefaction processes generally begins with the ground grain or similar material being mixed with cook and/or backset water, which can be sent from evaporation step 114 (FIG. 2), to create a slurry at slurry tank 130 whereat a commercial enzyme called alpha-amylase is typically added (not shown). The pH is adjusted here, as is known in the art, to about 5.2 to 5.8 and the temperature maintained between about 50° C. to 105° C. so as to allow for the enzyme activity to begin converting the insoluble starch in the slurry to soluble liquid starch. Other pH ranges, such as from pH 4.0-7.0, may be utilized and an acid treatment system using sulfuric acid, for example, can be used as well for pH control and conversion of the starches to sugars.

After the slurry tank 130, there are normally three optional pre-holding tank steps, identified in FIG. 3 as systems A, B, and C, which may be selected depending generally upon the desired temperature and holding time of the slurry. With system A, the slurry from the slurry tank 130 is subjected to a jet cooking step 132 whereat the slurry is fed to a jet cooker, heated to about 120° C., held in a U-tube or similar holding vessel for about 2 to about 30 minutes, then forwarded to a flash tank. In the flash tank, the injected steam flashes out of the liquid stream, creating another particle size reduction and providing a means for recovering the injected stream. The jet cooker creates a sheering force that ruptures the starch granules to aid the enzyme in reacting with the starch inside the granule and allows for rapid hydration of the starch granules. It is noted here that system A may be replaced with a wet grind system. With system B, the slurry is subjected to a secondary slurry tank step 134 whereat the slurry is maintained at a temperature from about 90° C. to 100° C. for about 10 min to about one hour. With system C, the slurry from the slurry tank 130 is subjected to a secondary slurry tank—no steam step 136, whereat the slurry from the slurry tank 130 is sent to a secondary slurry tank, without any steam injection, and maintained at a temperature of about 80° C. to 90° C. for about 1 to 2 hours. Thereafter, the slurry from each of systems A, B, and C is forwarded, in series, to first and second holding tanks 140 and 142 for a total holding time of about 60 minutes to about 4 hours at temperatures of about 80° C. to 90° C. to complete the liquefaction step 104, which then is followed by the saccharification and fermentation steps 106 and 108, along with the remainder of the process 100 of FIG. 2. While two holding tanks are shown here, it should be understood that one holding tank, more than two holding tanks, or no holding tanks may be utilized.

In today's typical grain to biofuel plants (e.g., corn to alcohol plants), many systems, particularly dry grind systems, process the entire corn kernel through fermentation and distillation. Such designs require about 30% more front-end system capacity because there is only about 70% starch in corn, with less for other grains and/or biomass materials. Additionally, extensive capital and operational costs are necessary to process the remaining non-fermentable components within the process. By removing undesirable, unfermentable components prior to fermentation (or other reaction process), more biofuel, biochemical and other processes become economically desirable.

It thus would be beneficial to provide an improved dry milling method and system that produces a cleaner sugar stream, such as for biofuel production, that may be similar to the sugar stream produced by conventional wet corn milling systems, but at a fraction of the cost and generate additional revenue from oil, protein and/or fiber yields, for example.

SUMMARY OF THE INVENTION

The present invention provides for a dry milling method and system that produces a cleaner sugar stream, such as for biofuel production, that may be similar to the sugar stream produced by conventional wet corn milling systems, but at a fraction of the cost, and generate additional revenue from oil, protein and/or fiber yields, for example.

In one embodiment of the invention, a method for producing a sugar stream is provided and includes mixing a ground grain and/or grain component with a liquid to produce a slurry including starch and unfermentable components. The method further includes subjecting the slurry to liquefaction followed by saccharification to convert the starch to simple sugars and produce a stream including the simple sugars and unfermentable components. After saccharification, but prior to further processing of the simple sugars, the method further includes separating the stream into a solids portion including unfermentable components and a liquid portion including the simple sugars, wherein the liquid portion defines a sugar stream having a dextrose equivalent of at least 20 D.E. and a total unfermentable solids fraction that is less than or equal to 30% of the total solids content.

In another embodiment of the invention, a method for producing a sugar stream is provided and includes mixing a ground grain and/or grain component with a liquid to produce a slurry including starch and unfermentable components. The method further includes subjecting the slurry to liquefaction followed by saccharification to convert the starch to simple sugars and produce a stream including the simple sugars and unfermentable components. After saccharification, but prior to a sugar conversion process, the method includes separating the stream into a solids portion, including unfermentable components and a liquid portion, including the simple sugars, wherein the liquid portion defines a sugar stream having a dextrose equivalent of at least 80 D.E. and a total unfermentable solids fraction that is less than or equal to 10% of the total solids content. The method further includes subjecting the sugar stream to the sugar conversion process.

In yet another embodiment of the invention, a system for producing a sugar stream is provided that includes a slurry tank in which ground grain and/or grain component mixes with a liquid to produce a slurry, including starch and unfermentable components, and a liquefaction and a saccharification system that receives the slurry and whereat the starch is converted to simple sugars thereby producing a stream including the simple sugars and unfermentable components. The system further includes a first separation device, which receives and separates the stream into a solids portion, including unfermentable components and a liquid portion, including the simple sugars, wherein the liquid portion defines a sugar stream having a dextrose equivalent of at least 20 D.E. and a total unfermentable solids fraction that is less than or equal to 30% of the total solids content and a biofuel and/or biochemical device that receives the sugar stream to produce biofuel and/or biochemicals from the simple sugars.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

Figure 1:
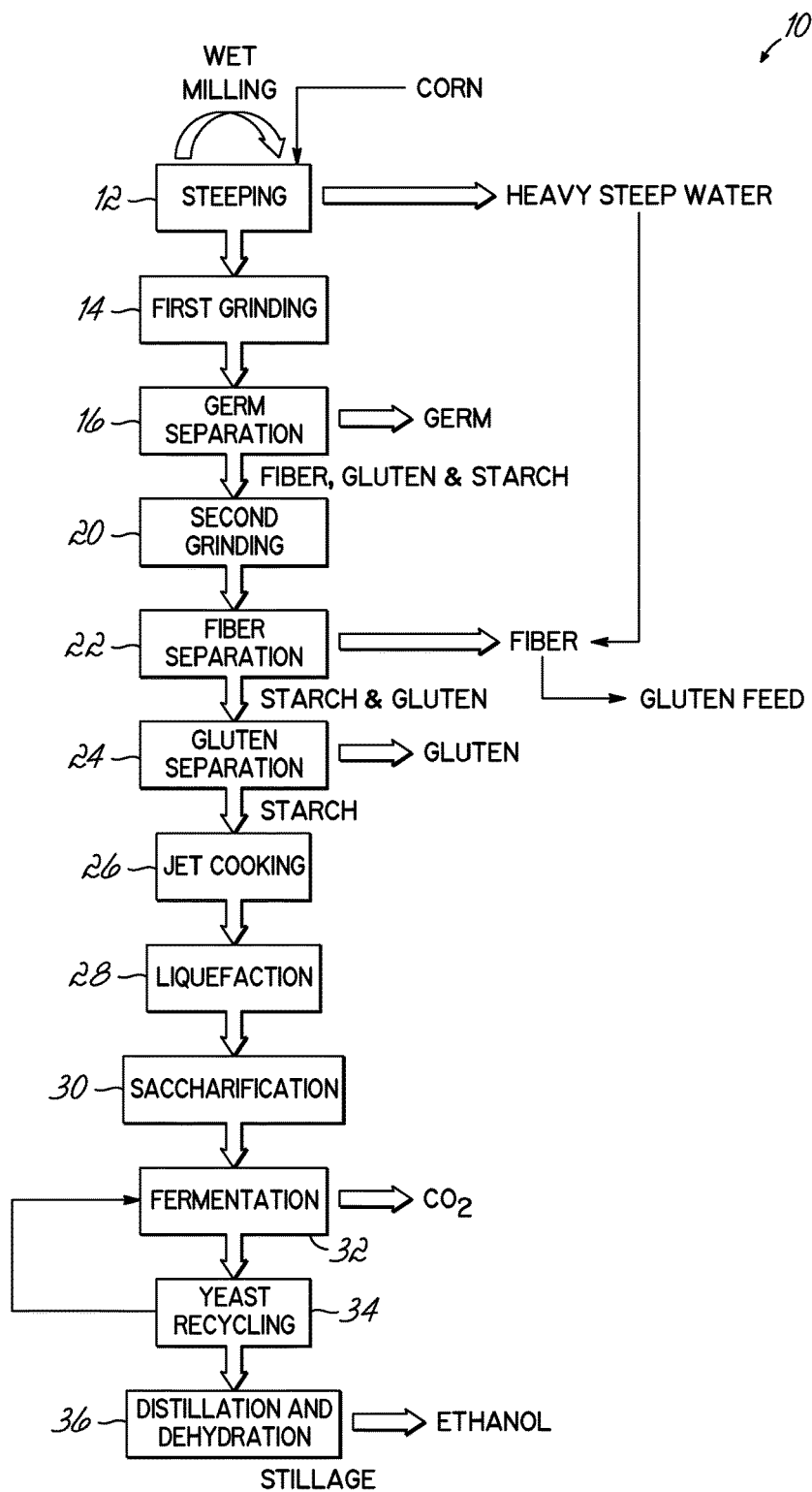
FIG. 1 is a flow diagram of a typical wet mill alcohol production process.
Figure 2:
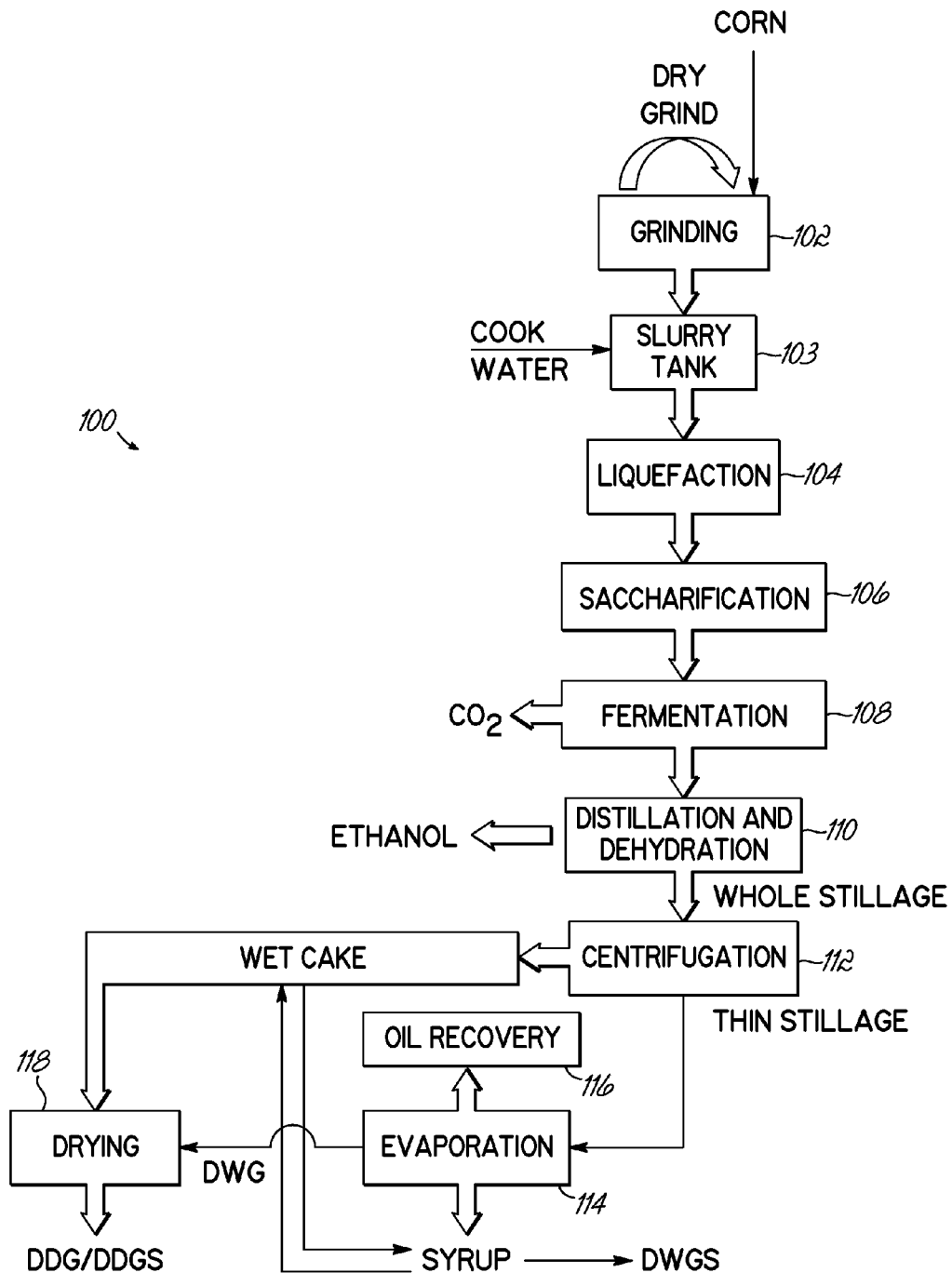
FIG. 2 is a flow diagram of a typical dry grind alcohol production process.
Figure 3:
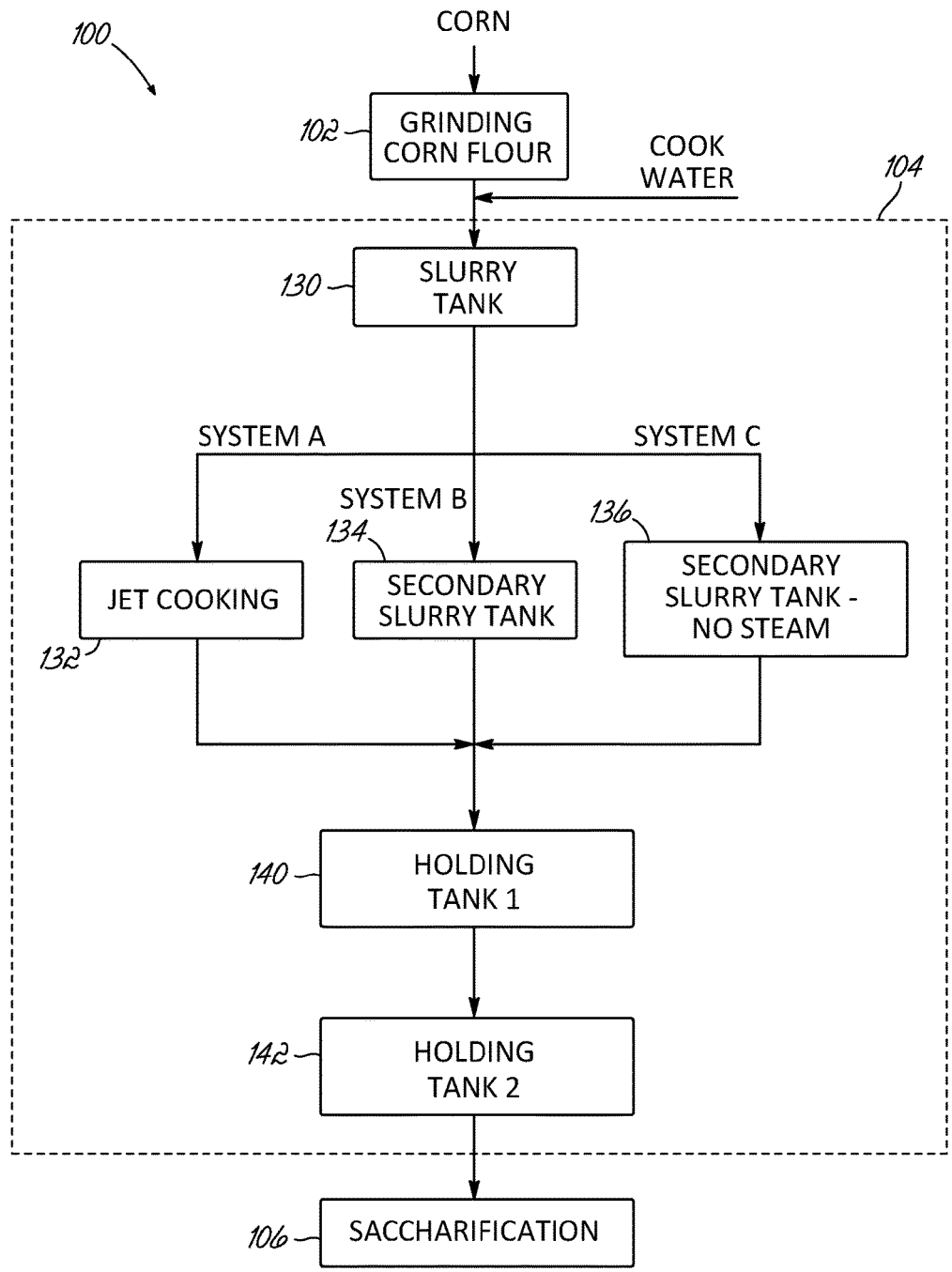
FIG. 3 is a flow diagram of various typical liquefaction processes in a typical dry grind alcohol production process.

FIGS. 1 and 2 have been discussed above and represent flow diagrams of a typical wet mill and dry grind alcohol production process, respectively. FIG. 3, likewise, has been discussed above and represents various typical liquefaction processes in a typical dry grind alcohol production process.

Figure 4:
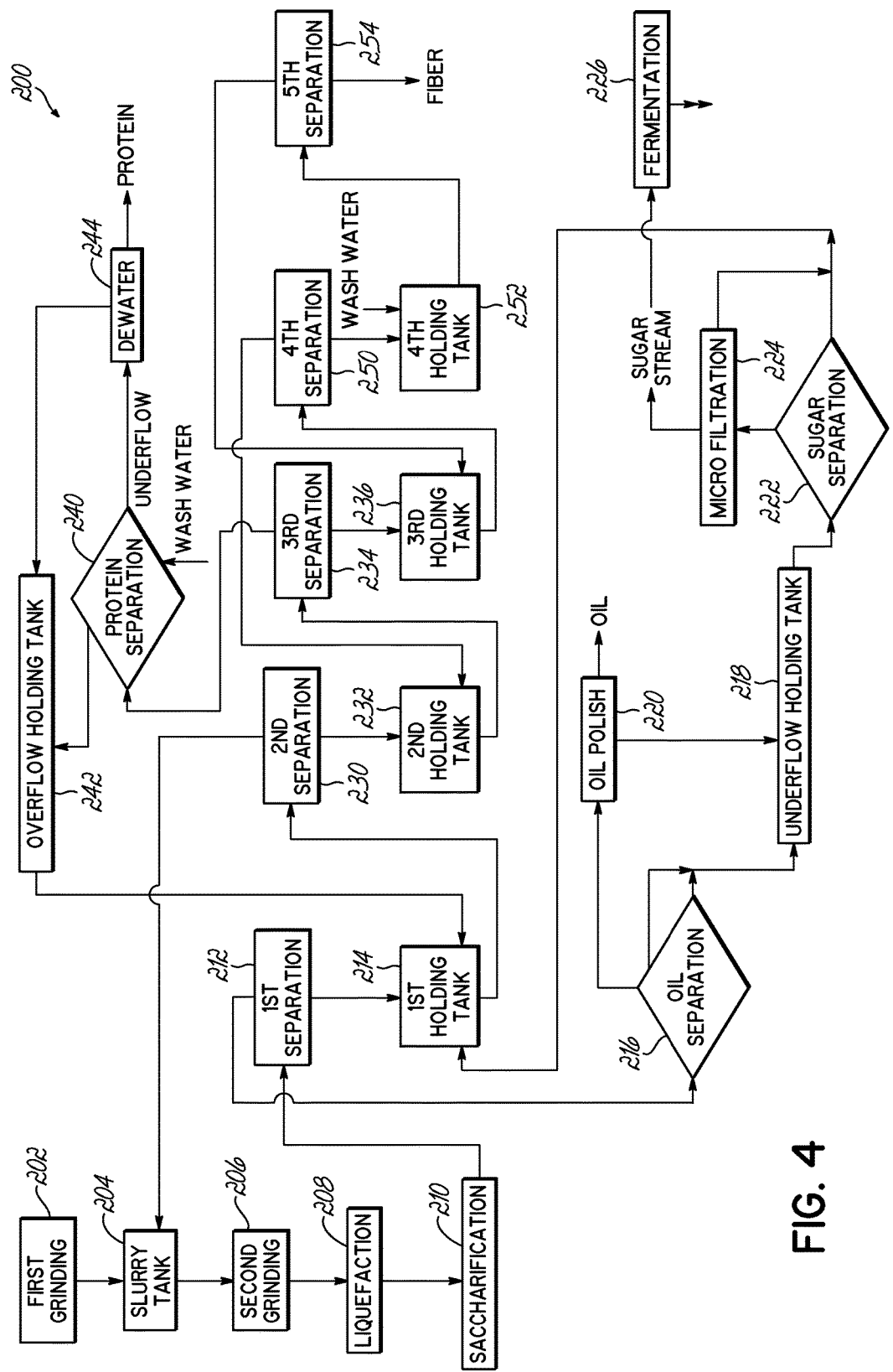
FIG. 4 is a flow diagram showing a dry grind system and method for producing a sugar stream in accordance with an embodiment of the invention.
Figure 5:
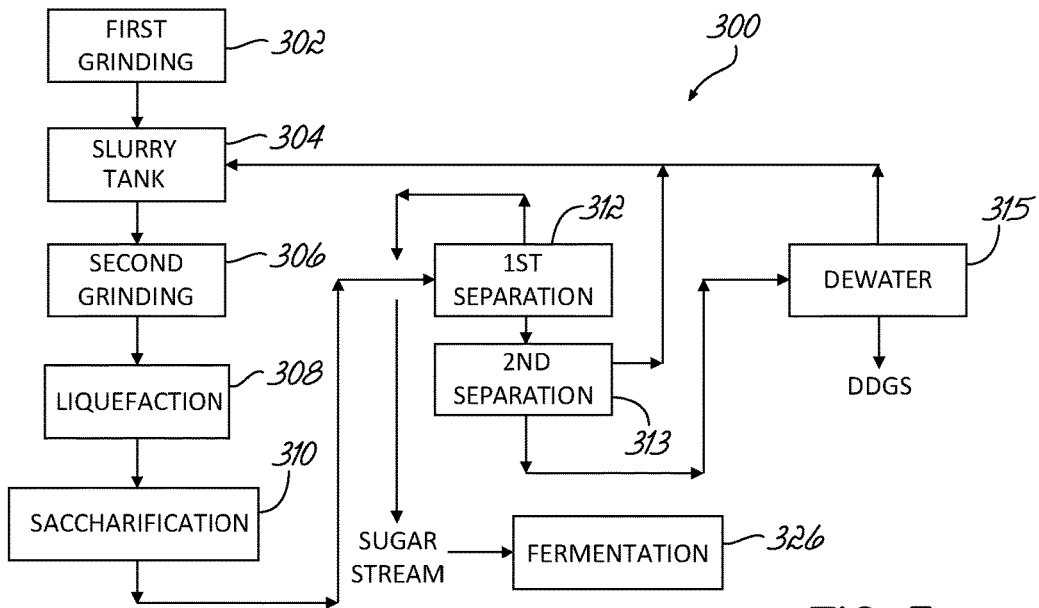
FIG. 5 is a flow diagram showing a dry grind system and method for producing a sugar stream in accordance with another embodiment of the invention.
Figure 6:
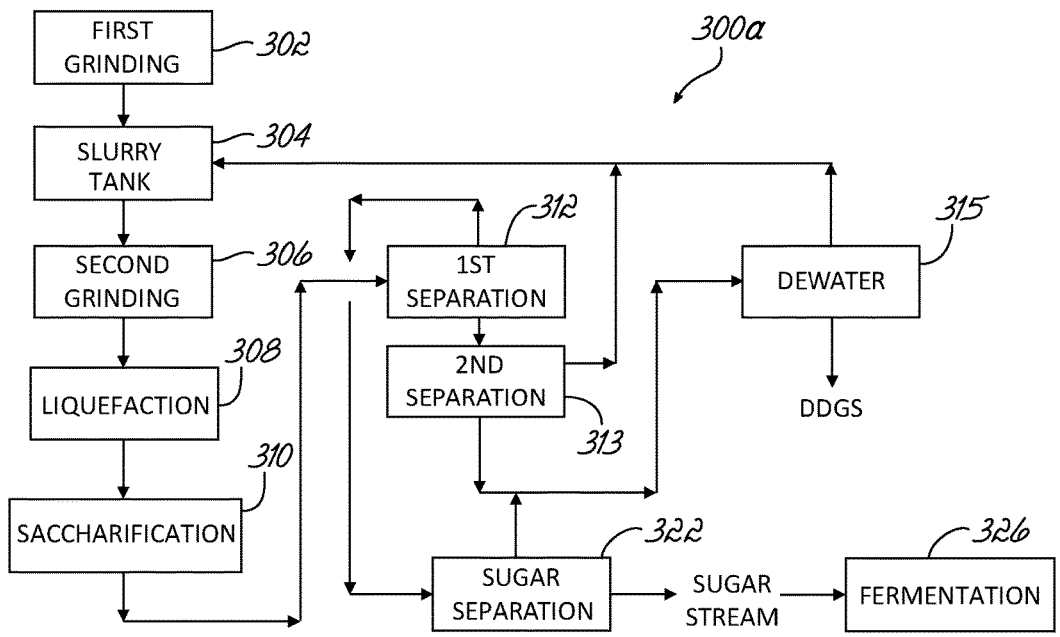
FIG. 6 is a flow diagram showing a dry grind system and method for producing a sugar stream in accordance with yet another embodiment of the invention.

FIGS. 4-6 illustrate embodiments of a dry grind system and method 200, 300, 300a for producing a sugar stream from grains or similar carbohydrate sources and/or residues, such as for biofuel production, in accordance with the present invention. As further discussed in detail below, a sugar/carbohydrate stream, which includes a desired Dextrose Equivalent (DE) where DE describes the degree of conversion of starch to dextrose (aka glucose) and/or has had removed therefrom an undesirable amount of unfermentable components, can be produced after saccharification and prior to fermentation (or other sugar conversion process), with such sugar stream being available for biofuel production, e.g., alcohol production, or other processes. In addition, the present systems and methods 200, 300, 300a also can involve the removal of certain grain components, e.g., corn kernel components, including protein, oil and/or fiber, prior to fermentation or other conversion systems, as further discussed below. In other words, sugar stream production and/or grain component separation occurs on the front end of the system and method 200, 300, 300a.

For purposes herein, in one example, the resulting sugar stream that may be desirable after saccharification, but before fermentation, such as for use in biofuel production, can be a stream where the starch/sugars in that stream define at least a 90 DE and/or where the total insoluble (unfermentable) solids fraction of the stream is less than or equal to 5% of the total solids content in the stream. In other words, at least 90% of the total starch/sugar in that stream is dextrose and/or no greater than 5% of the total solids in that stream includes non-fermentable components. In another example, the sugar stream may define at least 95 DE. In another example, the resulting sugar stream may define at least 98 DE. In yet another example, the starch/sugars in the stream can define at least a 20, 30, 40, 50, 60, 70, or 80 DE. In another example, the total insoluble (unfermentable) solids fraction of the stream is less than or equal to 3% of the total solids content in the stream. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In other words, the total fermentable content (fermentable solids fraction) of the stream may be no more than 30, 40, 50, 60, 70, 75, 80, 85, 90, 95, 97, or 99% of the total solids content in the stream. In another example, on a dry mass basis, the weight % fermentable material in the sugar stream that may be desired is greater than or equal to 80%. In another example, on a dry mass basis, the weight % fermentable material in a sugar stream is greater than or equal to 85%, 90%, 95%, 98%, or 99%.

In addition, although the system and method 200, 300, 300a described herein will generally focus on corn or kernel components, virtually any type of grain, whether whole and fractionated or any carbohydrate source, including, but not limited to, wheat, barley, sorghum, rye, rice, oats, sugar cane, tapioca, cassava or the like, as well as other biomass products, can be used. And broadly speaking, it should be understood that the entire grain or biomass or less than the entire grain, e.g., corn and/or grit and/or endosperm or biomass, may be ground and/or used in the system and method 200, 300, 300a.

With further reference now to FIG. 4, in this dry grind system and method 200, grains such as corn, for example, can be subjected to a first grinding step 202, which involves use of a hammer mill, roller mill, pin mill, impact mill, flaking mill or the like, to grind corn to particle sizes less than about 7/64 inch or, in another example, less than about 10/64 inch and allow for the release of oil therefrom. In one example, the screen size for separating the particles can range from about 24/64 inch to about 2/64 inch. In another example, the resulting particle sizes are from about 50 micron to 3 mm. The grinding also helps break up the bonds between the fiber, protein, starch and germ. In one example, screen size or resulting particle size may have little to no impact on the ability to separate the sugar from the remaining kernel or similar raw material component(s).

Next, the ground corn flour is mixed with backset liquid at slurry tank 204 to create a slurry. Optionally, fresh water may be added so as to limit the amount of backset needed here. The backset liquid includes overflow from a second separation step 230, which is a later step in the method 200 and is discussed further below. An enzyme(s), such as alpha amylase, optionally can be added to the slurry tank 204 or in a slurry blender (not shown) between steps 202 and 204. The slurry may be heated at the slurry tank 204 from about 66° C. (150° F.) to about 93° C. (200° F.) for about 10 minutes to about 120 minutes. The stream from the slurry tank 204 contains about 0.5 lb/bu free oil and about 1.5 lb/bu germ (particle size ranges from about 50 micron to about 3 mm), 1.8 lb/bu grit (particle size ranges from about 50 micron to about 3 mm), which can include starch and 4.2 lb/bu fiber (particle size ranges from about 50 micron to about 3 mm).

The stream from the slurry tank 204 next may be subjected to an optional second grinding/particle size reduction step 206, which may involve use of a disc mill or the like, to further grind the corn to particle sizes less than about 850 micron and allow for additional release of oil and protein/starch complexes therefrom. In another example, the particle sizes are from about 300 micron to 650 mm. The grinding further helps continue to break up the bonds between the fiber, protein and starch and facilitates the release of free oil from germ particles. Prior to subjecting the stream from the slurry tank to the second grinding/particle size reduction step 206, the slurry may be subjected to an optional dewatering step, which uses dewatering equipment, e.g., a paddle screen, a vibration screen, screen decanter centrifuge or conic screen centrifuge, a pressure screen, a preconcentrator, a filter press or the like, to remove a desired amount of liquids therefrom.

The further ground corn flour slurry or the stream from the slurry tank 204, if the second grinding step 206 is not provided, next is subjected to a liquefaction step 208, which itself can include multiple steps as discussed above and shown in FIG. 3. In one embodiment, the pH can be adjusted here to about 5.2 to 5.8 and the temperature maintained between about 50° C. to 105° C. so as to convert the insoluble starch in the slurry to soluble or liquid starch. Other pH ranges, such as from pH 4.0-7.0, may be utilized and an acid treatment system using sulfuric acid, for example, may be used as well for pH control and for conversion of the starches to sugars. The slurry may be further subjected to jet cooking whereat the slurry is fed to a jet cooker, heated to about 120° C., held for about 2 to 30 min., then forwarded to a flash tank. The jet cooker creates a sheering force that ruptures the starch granules to aid the enzyme in reacting with the starch inside the granule and for hydrating the starch molecules. In another embodiment, the slurry can be subjected to a secondary slurry tank whereat steam is injected directly to the secondary slurry tank and the slurry is maintained at a temperature from about 80° C. to 100° C. for about 30 min to one hour. In yet another embodiment, the slurry can be subjected to a secondary slurry tank with no steam. In particular, the slurry is sent to a secondary slurry tank without any steam injection and maintained at a temperature of about 80° C. to 90° C. for 1 to 2 hours. Thereafter, the liquefied slurry may be forwarded to a holding tank for a total holding time of about 1 to 4 hours at temperatures of about 80° C. to 90° C. to complete the liquefaction step 208. With respect to the liquefaction step 208, pH, temperature, and/or holding time may be adjusted as desired.

The slurry stream after the liquefaction step 208 has about 28%-36% dry solids (DS) content with all the components contained in the corn kernels, including starches/sugars, protein, fiber, germ, grit, oil and salts, for example. There generally are three types of solids in the liquefaction stream: fiber, germ and grit, which can include starch and protein, with all three solids having about the same particle size distribution. The stream from the liquefaction step 208 contains about 0.4 to about 0.6 lb/Bu free oil and about 1.5 lb/Bu germ particle (size ranges from less about 50 micron to about 1 mm), 4.5 lb/Bu protein (size ranges from about 50 micron to about 1 mm), and 4.25 lb/Bu fiber (particle size ranges from about 50 micron to about 3 mm). This stream next is sent to an optional saccharification step 210 whereat complex carbohydrate and oligosaccharides are further broken down into simple sugars, particularly single glucose sugar molecules (i.e., dextrose) to produce a liquefied mash.

In particular, at the saccharification step 210, the slurry stream may be subjected to a two-step cook process. The first part of the process, in one example, includes adjusting the pH to about 3.5 to 7.0, with the temperature being maintained between about 30° C. to 100° C. for 1 to 6 hours to further convert the insoluble starch in the slurry to soluble starch, particularly dextrose. In another example, the pH can be 5.2 to 5.8 or 5.5, for example. In another example, the temperature can be maintained at 80° C. for about 5 hours. Also, an enzyme, such as alpha-amylase may be added here. In one example, the amount of alpha-amylase may be from about 0.01 to about 0.04 wt % of the slurry stream. In another example, the amount of alpha-amylase may be from about 0.04 to about 0.1 wt % of the total stream.

The second part of the process, in one example, may include adjusting the pH to about 4.0 to 5.0, with the temperature being maintained between about 30° C. to 175° C. for about 2 to 5 hours so as to further convert the insoluble starch in the slurry to soluble starch, particularly dextrose. In another example, the pH can be 4.5. In another example, the temperature can be maintained from about 54° C. (130° F.) to 74° C. (165° F.) for about 4 hours or up to about 60 hours. An enzyme, such as glucoamylase, also may be added here. In one example, the amount of glucoamylase may be from about 0.01 to about 0.2 wt % of the slurry stream. In another example, the amount of glucoamylase may be from about 0.08 to about 0.14 wt % of the slurry stream. Other enzymes or similar catalytic conversion agents may be added at this step or previous steps that can enhance starch conversion to sugar or yield other benefits, such as fiber or cellulosic sugar release, conversion of proteins to soluble proteins, or the release of oil from the germ.

A liquefied sugar stream having a density of about 1.05 to 1.15 grams/cc can result here. At this point, the liquefied sugar stream, whether or not optionally subjected to the saccharification step 201, may be no less than about 90 DE. In another example, the liquefied sugar stream may be no less than 20, 30, 40, 50, 60, 70, or 80 DE. In this example, the liquefied sugar stream may not be considered desirable or "clean" enough, such as for use in biofuel or biochemical production, because the total fermentable content of the stream may be no more than 75% of the total solids content in the stream. In this example, the liquefied sugar stream can have a total solids fraction of about 28-36%, such solids including sugar, starch, fiber, protein, germ, oil and ash, for example. In yet another example, the total fermentable content of the stream is no more than 30, 40, 50, 60, or 70% of the total solids content in the stream. The remaining solids are fiber, protein, oil, and ash, for example.

After the optional saccharification step 210 (but before any potential fermentation or processing of the sugar stream), so as to provide a more desirable sugar stream, the liquefied sugar stream is subjected to a first separation step 212. If the optional saccharification step 210 is not provided here, the slurry stream from the liquefaction step 208 is sent to first separation step 212. The first separation step 212 filters a generally liquefied solution (about 60-80% by volume), which includes sugar, free oil, protein, fine solids, fiber, grit and germ, and which has a total solids fraction of about 28%, with a range of 20% to 40%, but higher or low solids fractions can be produced, but may not be economical here. In particular, the first separation step 212 uses dewatering equipment, e.g., a paddle screen, a vibration screen, screen decanter centrifuge or conic screen centrifuge, a pressure screen, a preconcentrator, a filter press or the like, to accomplish substantial separation of the solids portion, primarily fiber, germ, grit, which can include protein, from the liquid sugar portion, which primarily includes sugar (e.g., dextrose), oil and fine solids. The solids portion, which has a total solids fraction of about 39%, may be sent on to a first holding tank 214 and the liquid portion may be sent on and subjected to an optional oil separation step 216 to produce a cleaner, more desirable sugar stream, as further discussed below.

In one example, the dewatering equipment at the first separation step 212 is a paddle screen, which includes a stationary cylinder screen with high speed paddles with rakes. The number of paddles on the paddle screen can be in the range of 1 paddle per 4 to 8 inches or more of screen diameter. The number of paddles on the paddle screen can be modified depending on the amount of solids in the feed. The gap between the paddle screen and paddle can range from about 0.04 to 0.2 inch. A smaller gap gives a drier cake with higher capacity and purer fiber, but loses more fine fiber to the filtrate stream. A larger gap gives a wetter cake with lower capacity and purer liquid (less insoluble solid). The paddle speed can range from about 100 to 1,200 RPM. In another example, the paddle speed can range from 800 to 900 RPM. A higher speed provides higher capacity, but consumes more power. One suitable type of paddle screen is the FQ-PS32 paddle screen, which is available from Fluid-Quip, Inc. of Springfield, Ohio.

The screen for the dewatering equipment can include a wedge wire type with slot opening or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 25 micron to 450 micron. In another example, the size of the screen openings can range from about 25 micron to 300 micron. In another example, the screen openings can range from 40 to 85 micron. In yet another example, the screen openings are about 45 microns.

The now separated liquid portion or sugar stream from the first separation step 212 next can be subjected to an optional oil separation step 216, which can use any type of oil separator, such as a mud centrifuge, two or three phase decanter, disc decanter, two or three phase disc centrifuge, flotation tank, dissolved air floatation tank/system and the like, to separate oil from the sugar stream by taking advantage of density differences. In particular, the sugar stream is used as heavy media liquid to float oil/emulsion/fine germ particle. In this example, the oil separation step 216 can remove a small amount of solids so as to reduce the total solids fraction to about 27%. Other solid fraction ranges higher or lower can be achieved depending upon the starting solids feeding the oil separation step 216.

There can be two or three or more phases discharged from the oil separation step 216. As shown in FIG. 4, there are three phases with the first being a light phase, which primarily includes oil or an oil/emulsion layer. The second is an intermediate phase, which primarily includes sugars. The third phase is the solid phase, which primarily includes fine fiber, grit particle and protein. The underflow intermediate phase and solid phase can be combined as illustrated in FIG. 4 to produce a sugar stream, which may be forwarded to an underflow holding tank 218. If the optional oil separation step 216 is not present, the separated liquid portion or sugar stream from the first separation step 212 can be sent directly to holding tank 218. Alternatively, the separated liquid portion or sugar stream from the first separation step 212 can be sent on to fermentation step 226 to convert, e.g., via a fermentor, the sugar to alcohol, such as ethanol or butanol, or any other fermentation conversion process or similar sugar utilization process, as desired. If not initially provided after liquefaction step 208 as shown in FIG. 4, the saccharification step 210 may be provided just prior to fermentation step 226 or combined therewith so as to provide a single simultaneous saccharification and fermentation (SSF) step (not shown) to saccharify the sugar stream in a manner as discussed above.

The oil/emulsion layer can be forwarded to an optional oil polish step 220 whereat the layer can be subjected to centrifugation, including a three phase decanter, multi phase disc centrifuge or the like to separate pure oil from the emulsion and any fine germ particle. From the optional oil polish step 220, the emulsion and fine germ particle can be discharged as a heavy phase and returned to join up with the sugar stream from the oil separation step 216 at underflow holding tank 218. As another option, the emulsion and fine germ particle can be discharged as a heavy phase and returned to the oil separation step 216. As an additional option, the emulsion and fine germ particle can be joined up with either the liquefied sugar stream from the saccharification step 210 prior to the first separation step 212 or the solids portion from the first separation step 212. At the oil polish step 220, alcohol, such as 200 proof alcohol from a distillation tower from a later distillation step (not shown), as known in the art, can be added to the emulsion and fine germ particles so as to break the emulsion and extract oil from the fine germ particle, which normally are less than 100 micron.

The oil that is recovered at step 220 has a much more desirable quality in terms of color and free fatty acid content (less than 7% and, in another example, less than 5%) as compared to oil that is recovered downstream, particularly oil recovered after fermentation, such as on the back end. In particular, the color of pre-fermentation recovered oil is lighter in color and lower in free fatty acid content. The oil yield at step 220 can reach about 0.9 lb/bu. The recovered oil here can be about 95.5% oil and, in another example, the oil can be 99% oil.

Returning now to the sugar stream at holding tank 218, this stream is sent on to a sugar separation step 222, which can include a clarifier, filtration centrifuge or the like, to separate heavier components, including residual protein, from the sugar stream. At this point, the separated sugar stream may be no less than about 90 DE. In another example, the liquefied sugar stream may be no less than 20, 30, 40, 50, 60, 70, or 80 DE. In this example, the sugar stream here may be considered desirable or "clean" enough, such as for use in biofuel production, because the total insoluble (unfermentable) solids fraction of the stream is less than or equal to 5% of the total solids of the stream. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to sugar separation step 222 may have a total solids fraction of 27%, such solids including sugar, starch, fiber, protein and/or germ, for example.

After the sugar separation step 222, the sugar stream may then be further subjected to an optional microfiltration (or similar filtration) step 224, which can include a micro-filter, membrane filtration, precoat/diatomaceous earth filter or the like, to produce a more desirable sugar stream, which may be considered a purified or refined sugar stream, by further separating out any remaining insoluble components, color, ash, minerals or the like. In one example, the filter screen size here may be from about 5 to 100 microns. In another example, the filter screen size may be from about 8 to 50 microns. Due to the input of water, the sugar stream can have a total solids fraction of 20-27%. In this example, the sugar stream here may be considered purified or refined enough because the total insoluble (unfermentable) solids fraction of the stream is less than 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%.

The microfiltration step 224 may be replaced by, or additionally include, ultrafiltration, carbon column color removal, filter press, flotation and/or demineralization technologies (e.g., ion exchange). Resin refining, which includes a combination of carbon filtration and demineralization in one step, can also be utilized for refining the sugars. Additionally, due to a low solids content of the sugar stream here, an optional evaporation step (not shown) may be added hereafter to further concentrate the total solids fraction. The heavy components from the sugar separation step 222 and microfiltration step 224 can be combined together and sent back to meet up with the solids portion at the first holding tank 214 or optionally may be recycled back to meet up with the separated liquid portion or sugar stream from the first separation step 212, such as prior to the optional oil separation step 216, to be again sent through the sugar separation step 222 and optional microfiltration step 224. These heavier components or underflow, can be more concentrated in total solids, at 28%.

The sugar stream from the microfiltration step 224 can be sent on to fermentation step 226 to convert, e.g., via a fermentor, the sugars to alcohol, such as ethanol or butanol or any other fermentation conversion process or similar sugar utilization process, followed by distillation and/or separation of the desired component(s) (not shown), which can recover the alcohol or byproduct(s)/compound(s) produced, as is known in the art. If not initially provided after liquefaction step 208 earlier in the system and method 200, as is shown in FIG. 4, the optional saccharification step 210 may be provided just prior to fermentation step 226, here or combined therewith, so as to provide a single simultaneous saccharification and fermentation (SSF) step (not shown) so as to subject the sugar stream to saccharification in a manner as discussed above. The sugar stream can allow for recovery of a fermentation agent from the fermentation step 226. The fermentation agent can be recovered by means known in the art and can be dried as a separate product or, for example, can be sent to the protein separation step 240 or other streams/steps, in the method and system 200, which can allow for capture of the fermentation agent and/or used for further processing. Fermentation agent (such as yeast or bacteria) recycling can occur by use of a clean sugar source. Following distillation or desired separation step(s), the system and method 200 can include any back end type process(es), which may be known or unknown in the art to process, for example, the whole stillage. The fermentation step 226 may be part of an alcohol production system that receives a sugar stream that is not as desirable or clean, i.e., "dirtier," than the sugar stream being sent and subjected to the same fermentation step 226 as the dirty sugar stream. Other options for the sugar stream, aside from fermentation, can include further processing or refining of the glucose to fructose or other simple or even complex sugars, processing into feed, microbe based fermentation (as opposed to yeast based) and other various chemical, pharmaceutical or nutriceutical processing (such as propanol, isobutanol, citric acid or succinic acid) and the like. Such processing can occur via a reactor, which can include a fermentor.

Returning now to the first holding tank 214, the dewatered solids portion of the stream (about 70 to 25% water) next can be subjected to a second separation step 230. And as with the first separation step 212, the second separation step 230 uses dewatering or filtration equipment, e.g., a paddle screen, a vibration screen, a filtration, scroll screen or conic screen centrifuge, a pressure screen, a preconcentrator and the like, to accomplish further separation of the solids portion, primarily fiber, grit, which can include protein and germ from the liquid portion, which primarily includes sugar, oil and fine solids. In one example, the dewatering equipment is a paddle screen, as above described. In one example, the screen size used in the second separation step 230 can range from 25 micron to 150 micron. In another example, the screen openings can range from 40 to 85 micron. In yet another example, the screen openings are about 45 microns. With the second separation step 230, the actual screen openings may be larger in size than those in the first separation step 212.

The resulting solids portion from the second separation step 230 is sent on to a second holding tank 232 and the liquid portion or filtrate, may be joined up with the ground corn flour at slurry tank 204 as part of a counter current washing setup. The resulting solids portion has a total solids fraction of about 35%, with the filtrate having a total solids fraction of about 26%. The filtrate can contain particles (germ, grit, fine fiber and protein) having sizes smaller than the screen size openings used in the second separation step 230.

From the second holding tank 232, the wet cake or dewatered solids portion of the stream can be subjected to a third separation step 234. The third separation step 234 uses dewatering equipment, e.g., a paddle screen, a vibration screen, a filtration, scroll screen or conic screen centrifuge, a pressure screen, a preconcentrator, a press and the like, to accomplish further separation of the solids portion, primarily fiber, germ, grit, which can include protein from the liquid portion, which primarily includes sugar, oil and fine solids. In one example, the dewatering equipment is a paddle screen, as above described. With the third separation step 234, the actual screen openings may be larger in size than those in the second separation step 230. In one example, the screen size used in the third separation step 234 can range from 100 micron to 500 micron. In another example, the screen openings can range from 150 to 300 micron. In yet another example, the screen openings are about 200 microns. Alternatively, the actual screen openings may be smaller in size than those in the second separation step 230.

The resulting solids portion from the third separation step 234 is sent on to a third holding tank 236 and the overflow liquid portion or filtrate may be sent to a protein separation step 240, which uses, for example, a clarifier, filtration centrifuge, decanter, stack disc centrifuge or the like, to separate the liquid portion of the stream from a heavier protein portion. Due to the removal of solids throughout the "washing" process, the total solids fraction in the solids stream at the third holding tank 236 is about 26%. The filtrate has a total solids fraction of about 22%. The clarifier, for example, can be provided with washing capabilities so that wash water can be supplied thereto. The additional wash water allows for easier separation of the overflow liquid portion into a heavier protein portion and liquid portion. The heavier protein portion separates from the overflow liquid portion and is removed as the underflow whereas the lighter liquid portion can be removed as the overflow. Additionally, a two or three phase separation device can be utilized for this step. The overflow liquid portion contains about 18% total solids and is sent to an overflow holding tank 242. In another embodiment, prior to being sent to the protein separation step 240, the overflow liquid portion or filtrate from the third separation step 234 can be subjected to an optional liquefaction step whereat additional carbohydrates, including starches, can be converted to sugars so that the protein portion can be further concentrated up at the protein separation step 240.

The underflow protein portion next can be sent to an optional dewatering step 244 whereat the protein portion can be subjected to filtration, including microfiltration or vacuum filtration, such as via a rotary vacuum filter or the like. In an alternate embodiment, the protein portion can be dewatered by being subjected to a decanter centrifuge or the like, as are known in the art. In another embodiment, prior to being sent to the dewatering step 244, the underflow protein portion can be subjected to an optional liquefaction step whereat additional carbohydrates, including starches, can be converted to sugars, allowing for the underflow protein portion to be further concentrated up at the dewatering step 244. The filtrate from the dewatering step 244 can be returned to overflow holding tank 242 and joined up with the overflow liquid portion from protein separation step 240. The combined filtrate at overflow holding tank 242 can be sent back to the first holding tank 214 as part of the counter current washing process. In another option, the combined filtrate at overflow holding tank 242 may be joined up with the ground corn flour at slurry tank 204, and the liquid portion or filtrate from the second separation step 230 can be sent back to the first holding tank 214 as part of the counter current washing setup. Due to the various dewatering options, the total solids fraction of the final dewatered protein can vary between 20 and 36%.

The dewatered protein then may be dried, such as by being sent to a dryer (not shown), as is known in the art. The final dried protein product can define a high protein corn meal that includes at least 40 wt % protein on a dry basis and which may be sold as pig or chicken feed, for example. In another embodiment, the high protein corn meal includes at least 45 wt % protein on a dry basis. In another embodiment, the high protein corn meal includes at least 50 wt % protein on a dry basis. In yet another embodiment, the high protein corn meal includes at least 60 wt % protein on a dry basis. In still another embodiment, the high protein corn meal includes at least 62 wt % protein on a dry basis and is referred to as a corn gluten meal product. In addition, the recovered protein can be used as a feed source to separate the zein proteins or can be further refined to remove individual amino acids (such as lysine or other key limiting amino acid). One exemplary zein separation process for the recovered feed source corn protein is shown and described in Cheryan, U.S. Pat. No. 6,433,146, the contents of which are incorporated herein by reference. It is noted that as the protein purity increases, the yield decreases such that the yield is variable based on the end product. In other examples, the recovered protein can be used as a fertilizer and/or a natural herbicide or further purified to utilize for isolate proteins. To yield isolate proteins, in one example, the protein underflow stream may be passed through a solvent extraction process (e.g., alcohol generally or ethanol and water) (not shown) to remove all starches, sugars and other components. Additionally the separated proteins can be used as a food source or a flavor carrier or for health and beauty aids.

From the third holding tank 236, the wet cake or dewatered solids portion of the stream next can be subjected to a fourth separation step 250. The fourth separation step 250 uses dewatering equipment, e.g., a paddle screen, a vibration screen, a filtration, scroll screen or conic screen centrifuge, a pressure screen, a preconcentrator and the like, to accomplish further separation of the solids portion, primarily fiber, germ, grit, which can include protein from the liquid portion, which primarily includes sugar, oil and fine solids. In one example, the dewatering equipment is a paddle screen, as above described. In one example, the screen size used in the fourth separation step 250 can range from 100 micron to 500 micron. In another example, the screen openings can range from 150 to 300 micron. In yet another example, the screen openings are about 200 microns. With the fourth separation step 250, the actual screen openings may be larger in size than those in the third separation step 234.

The resulting solids portion from the fourth separation step 250 is sent on to a fourth holding tank 252 and the liquid portion or filtrate, may be sent to the second holding tank 232 as part of the counter current washing operation. The resulting solids portion has a total solids fraction of 20%. The filtrate has a total solids content of 14%. Alternatively, the filtrate may be sent to protein separation step 240 and the filtrate from the third separation step 234 may be sent to the second holding tank 223 in a counter current washing operation. The filtrate from the fourth separation step 250 contains particles having sizes smaller than the screen size openings used in the fourth separation step 302. Wash water can be supplied here to the fourth holding tank 252.

From the fourth holding tank 252, the wet cake or dewatered solids portion of the stream next, which has been further diluted via the addition of wash water, can be subjected to a fifth separation step 254 whereat dewatering equipment, e.g., a paddle screen, vibration screen, filtration centrifuge, pressure screen, screen bowl decanter and the like, is used to accomplish separation of the solid portion, which includes fiber from the liquid portion. The additional wash water here allows for easier separation of the stream into primarily a fiber portion and an overflow liquid portion. One exemplary filtration device for the fifth separation step 254 is shown and described in Lee, U.S. Pat. No. 8,813,973, the contents of which are incorporated herein by reference. The screen openings in this step normally will be about 500 microns to capture amounts of tip cap, pericarp, as well as fine fiber, but can range from about 400 micron to about 1500 micron. Residual liquid from the fifth separation step 254 may be sent to the third holding tank 236 as part of the counter current washing process. The dewatered fiber contains less than 3% starch (with a range from 0.5-9%) as compared with normal dry mill fiber, which has about 4 to 6% starch in fiber. The % protein in the fiber also decreases from a conventional 29% to about 12%, with a range from about 6% to about 22%, and the % oil decreases from a conventional 9% to about 2-4%, with a range from about 1% to about 5%.

The resulting wet cake fiber portion from the fifth separation step 254 may be further dried by a drier, as is known in the art. This wet cake fiber portion has a total solids fraction of approximately 38 to 44%. The wet cake fiber portion can be used as feed stock for secondary alcohol or other chemical or feed or food production. The resulting cellulosic material, which includes pericarp and tip cap, and has more than about 35% DS, less than about 10% protein, less than about 2% oil, and less than about 1% starch/sugar, can be sent to a secondary alcohol system, as is known in the art, as feed stock without any further treatment. The cellulose fiber yield is about 3 lb/bu. The fiber may also be burned in a biomass boiler system or used to produce a typical DDGS type product, for example. Additionally the separated fiber stream can be used for furfural production or for further processing into other chemical, food, pharmaceutical and/or nutriceutical usages/applications.

While five separation steps 212, 230, 234, 250, 254 and four holding tanks 214, 232, 236, 252 are shown and utilized here, it should be understood that this system and method 200 may be modified to accommodate less than or more than that shown for recovering the sugar stream, oil, protein and/or fiber, with desirable yields and/or purity. For example, the system and method 200 can eliminate up to four of the separation steps and up to three of the holding tanks. In another example, at least three of the separation steps are utilized. In another example, at least four of the separation steps are utilized. Due to the sequential separation steps 212, 230, 234, 250, 254, sugars, starch, protein and oil can be systematically washed off the fiber so that the fiber can be concentrated at the last separation step, e.g., the fifth separation step 254, and the other components recovered and separated out, as desired. In another example, multiple separation steps and holding tanks may be replaced by one or more filtration centrifuges, which include multiple washing stages in a single centrifuge.

Also, further modifications can be made to the above system and method 200 to improve co-product recovery, such as oil recovery using surfactants and other emulsion-disrupting agents. In one example, emulsion-disrupting agents, such as surfactants, may be added prior to steps in which emulsions are expected to form or after an emulsion forms in the method. For example, emulsions can form during centrifugation such that incorporation of surfactants prior to or during centrifugation can improve oil separation. In one example, the syrup stream pre-oil separation can also have emulsion breakers, surfactants, and/or flocculants added to the evaporation system to aid in enhancing the oil yield. This may result in an additional 0.05 to 0.5 lb./bu oil yield gain.

With reference now to FIG. 5, a dry grind system and method 300 for producing a sugar stream from grains or similar carbohydrate sources and/or residues, such as for biofuel production, in accordance with another embodiment of the invention is shown. As further discussed below, a sugar stream, which includes a desired dextrose equivalent and/or has had removed therefrom an undesirable amount of unfermentable components, can be produced after saccharification and prior to fermentation (or other sugar conversion process), with such sugar stream being available for biofuel production, e.g., alcohol production or other processes. Here, in certain respects, system and method 300 is a simplified embodiment of the system and method 200 of FIG. 4, including the absence of separation and recovery of front end oil and protein, for example.

As shown now in FIG. 5, system and method 300, like the system and method 200 of FIG. 4, includes a first grinding step 302 whereat grains, such as corn, for example, can be subjected to grinding so that the corn is ground into corn flour. The ground corn flour is mixed with backset liquid at slurry tank 304 to create a slurry. Optionally, fresh water may be added so as to limit the amount of backset needed here. The backset liquid includes overflow from a dewatering step 315, which is a later step in the system and method 300, and is discussed further below.

The stream from the slurry tank 304 next may be subjected to an optional second grinding step 306, which involves use of a disc mill or the like, to further grind the corn. Also, prior to subjecting the stream from the slurry tank to the second grinding/particle size reduction step 306, the slurry may be subjected to an optional dewatering step, which uses dewatering equipment, e.g., a paddle screen, a vibration screen, screen decanter centrifuge or conic screen centrifuge, a pressure screen, a preconcentrator, a filter press or the like, to remove a desired amount of liquids therefrom. The further ground corn flour slurry or the stream from the slurry tank 304, if the second grinding step 306 is not provided, next is subjected to liquefaction step 308, which itself can include multiple steps as discussed above and shown in FIGS. 3 and 4. The stream from the liquefaction step 308 is sent to an optional saccharification step 310 whereat complex carbohydrate and oligosaccharides are further broken down into simple sugars, particularly single glucose sugar molecules (i.e., dextrose) to produce a liquefied mash. In particular, at the saccharification step 310, the slurry stream may be subjected to a two-step cook process, as already discussed in detail above.

A liquefied sugar stream having a density of about 1.05 to 1.15 grams/cc can result here. At this point, the liquefied sugar stream, whether or not optionally subjected to the saccharification step 310, may be no less than about 90 DE. In another example, the liquefied sugar stream may be no less than 20, 30, 40, 50, 60, 70, or 80 DE. In this example, the liquefied sugar stream may not be considered desirable or "clean" enough, such as for use in biofuel or biochemical production because the total fermentable content of the stream may be no more than 75% of the total solids content in the stream. In this example, the liquefied sugar stream can have a total solids fraction of about 28-36%, such solids including sugar, starch, fiber, protein, germ, oil, and ash, for example. In yet another example, the total fermentable content of the stream is no more than 30, 40, 50, 60, or 70% of the total solids content in the stream. The remaining solids are fiber, protein, oil and ash, for example.

After the optional saccharification step 310 (but before any potential fermentation or sugar processing of the sugar stream), so as to provide a more desirable sugar stream, the liquefied sugar stream is subjected to a first separation step 312. If the optional saccharification step 310 is not provided here, the slurry stream from the liquefaction step 308 is sent to first separation step 312. The first separation step 312 filters a generally liquefied solution (about 60-80% by volume), which includes sugar, free oil, protein, fine solids, fiber, grit and germ, and which has a total solids fraction of 28%. In particular, the first separation step 312 uses dewatering equipment, e.g., a paddle screen, a vibration screen, screen decanter centrifuge or conic screen centrifuge, a pressure screen, a preconcentrator or the like, to accomplish substantial separation of the solids portion, primarily fiber, germ, grit, which can include protein from the liquid sugar stream, which primarily includes sugar, oil, and fine solids. As an alternative option, the liquefied sugar stream from the saccharification step 310 can be subjected to a solids concentration process, such as an evaporation step (not shown), which can concentrate the solids via evaporation prior to the first separation step 312.

At this point, the separated sugar stream may be no less than about 90 DE. In another example, the liquefied sugar stream may be no less than 20, 30, 40, 50, 60, 70, or 80 DE. In this example, the sugar stream here may be considered desirable or "clean" enough, such as for use in biofuel production, because the total insoluble (unfermentable) solids fraction of the stream is less than or equal to 5% of the total solids in the stream. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to sugar separation step 222 may have a total solids fraction of 27%, such solids including sugar, starch, fiber, protein, and/or germ, for example.

The solids portion or wet cake, which has a total solids fraction of about 39%, may be sent on to an optional second separation step 313, and the sugar stream can be sent on to fermentation step 326 to convert, e.g., via a fermentor, the sugar to alcohol, such as ethanol or butanol or any other fermentation conversion process or similar sugar utilization process, followed by distillation and/or separation of the desired component(s) (not shown), which recovers the alcohol or byproduct(s)/compound(s) produced, as is known in the art. If not initially provided after liquefaction step 308 earlier in the system and method 300, as is shown in FIG. 5, the optional saccharification step 310 may be provided just prior to fermentation step 326 here or combined therewith so as to provide a single simultaneous saccharification and fermentation (SSF) step (not shown) so as to subject the sugar stream to saccharification in a manner as discussed above. The sugar stream also can allow for recovery of a fermentation agent from the fermentation step 326. Fermentation agent (such as yeast or bacteria) recycling can occur by use of a clean sugar source. The fermentation agent can be recovered by means known in the art and can be dried as a separate product, for example or can be sent to other streams/steps in the method and system 300, which can allow for capture of the fermentation agent and/or used for further processing. Following distillation or desired separation step(s), the system and method 300 can include any back end type process(es), which may be known or unknown in the art to process, for example, the whole stillage. The fermentation step 326 may be part of an alcohol production system that receives a sugar stream that is not as desirable or clean, i.e., "dirtier," than the sugar stream being sent and subjected to the same fermentation step 326 as the dirty sugar stream. Other options for the sugar stream, aside from fermentation, can include further processing or refining of the glucose to fructose or other simple or even complex sugars, processing into feed, microbe based fermentation (as opposed to yeast based) and other various chemical, pharmaceutical or nutriceutical processing (such as propanol, isobutanol, citric acid, or succinic acid) and the like. Such processing can occur via a reactor, which can include a fermentor.

Returning now to the solids portion from the first separation step 312, the solids portion can be subjected to optional second separation step 313 whereat dewatering equipment, e.g., a paddle screen, vibration screen, filtration centrifuge, pressure screen, screen bowl decanter and the like, is used to accomplish further separation of the solid portion or wet cake, which includes fiber from the liquid portion. An optional addition of wash water at the second separation step 313 can allow for easier separation of the solids portion into primarily a fiber portion and an overflow liquid portion. One exemplary filtration device for the second separation step 313 is shown and described in Lee, U.S. Pat. No. 8,813,973, the contents of which are incorporated herein by reference. The overflow liquid portion from the second separation step 313 may be sent back to the slurry tank 304, the liquefaction step 308 or the saccharification step 310, as well as at other points within the overall system and method 300. Further refinements of the wet cake to separate out individual components can be utilized as previously discussed above.

In one example and with further reference to FIG. 5, the wet cake next can be sent to an optional dewatering step 315 whereat the wet cake portion can be subjected to filtration or the like. In an alternate embodiment, the wet cake can be dewatered by being subjected to a decanter centrifuge or the like, as are known in the art. The filtrate from the dewatering step 315 can be returned to the slurry tank 304 or the saccharification step 310, as well as at other points within the overall system and method 300. The dewatered wet cake, whether or not subjected to optional steps 312, 315, may be dried, such as by being sent to a dryer (not shown), as is known in the art, to produce a DDGS type product, for example.

Here, the system and method 300 has been designed such that a sugar solution is provided along with a separate mixture of sugar/starch, germ, oil, grit, fiber and protein, which combine to produce a product similar to the traditional DDGS product. without any fermentation agent. The fermentation agent from a sugar stream fermentation process may be separated and added to this combined DDGS like product. The fermentation agent may be recovered by means known in the art and may be dried as a separate product. The fermentation agent also can be recycled or sent to other streams/steps in the method and system 300, which can allow for capture of the fermentation agent and/or can be used for further processing. Additionally, this combined DDGS like stream has some fermentable starch/sugar contained therein, which can be fermented or further processed as desired.

In an alternate embodiment as shown in FIG. 6, system and method 300a, like the system and method 300 of FIG. 5, optionally includes a sugar separation step 322 whereat the sugar stream from the first separation step 312 can be subjected to a clarifier, filtration centrifuge or the like, to separate heavier components, including residual protein, from the sugar stream. At this point, the separated sugar stream may be no less than about 90 DE. In another example, the liquefied sugar stream may be no less than 20, 30, 40, 50, 60, 70, or 80 DE. In this example, the sugar stream here may be considered desirable or "clean" enough, such as for use in biofuel production, because the total insoluble (unfermentable) solids fraction of the stream is less than or equal to 5% of the total solids of the stream. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In this example, the stream sent to sugar separation step 222 may have a total solids fraction of 27%, such solids including sugar, starch, fiber, protein and germ, for example.

The overflow portion from the sugar separation step 322 may be sent back to join up with the solids portion or wet cake from the first or second separation steps 312 or 313, the second separation step 313, the slurry tank 304 or the saccharification step 310, as well as at other points within the overall system and method 300a. After the sugar separation step 322, the sugar stream may then be further subjected to optional separation steps, such as those shown in FIG. 4, including optional microfiltration (or similar filtration) steps, etc. The resulting sugar stream from the sugar separation step 322 (or other optional steps) can be sent on to fermentation step 326, as above described, to convert, e.g., via a fermentor, the sugar to alcohol, such as ethanol or butanol or any other fermentation conversion process or similar sugar utilization process, followed by distillation and/or separation of the desired component(s) (not shown), which recovers the alcohol or byproduct(s)/compound(s) produced, as is known in the art. If not initially provided after liquefaction step 308 earlier in the system and method 300a, as is shown in FIG. 6, the optional saccharification step 310 may be provided just prior to fermentation step 326 here or combined therewith so as to provide a single simultaneous saccharification and fermentation (SSF) step (not shown) so as to subject the sugar stream to saccharification in a manner as discussed above. The sugar stream also can allow for recovery of a fermentation agent from the fermentation step 326. Fermentation agent (such as yeast or bacteria) recycling can occur by use of a clean sugar source. The fermentation agent can be recovered by means known in the art and can be dried as a separate product, for example or can be sent to other streams/steps in the method and system 300a, which can allow for capture of the fermentation agent and/or used for further processing. Following distillation or desired separation step(s), the system and method 300 can include any back end type process(es), which may be known or unknown in the art to process, for example, the whole stillage. The fermentation step 326 may be part of an alcohol production system that receives a sugar stream that is not as desirable or clean, i.e., "dirtier," than the sugar stream being sent and subjected to the same fermentation step 326 as the dirty sugar stream. Other options for the sugar stream, aside from fermentation, can include further processing or refining of the glucose to fructose or other simple or even complex sugars, processing into feed, microbe based fermentation (as opposed to yeast based), and other various chemical, pharmaceutical or nutriceutical processing (such as propanol, isobutanol, citric acid, or succinic acid) and the like. Such processing can occur via a reactor, which can include a fermentor.

While the present invention has been illustrated by a description of various embodiments and while these embodiments have been described in considerable detail, it is not the intention of the applicant to restrict or in any way limit the scope of the appended claims to such detail. For example, various enzymes (and types thereof) such as amylase, alpha-amylase, or glucoamylase, fungal, cellulase, cellobiose, protease, phytase and the like can be optionally added, for example, before, during, and/or after any number of steps in the systems and methods 200, 300, 300a, including the slurry tank 204, 304, the second grinding step 206, 306, the liquefaction step 208, 308, and/or the saccharification step 210, 310, such as to enhance the separation of components, such as to help break the bonds between protein, starch, and fiber and/or to help convert starches to sugars and/or help to release free oil. In addition, temperature, pH, surfactant and/or flocculant adjustments may be adjusted, as needed or desired, at the various steps throughout the system and method 200, 300, 300a, including at the slurry tank 204, 304, etc., such as to optimize the use of enzymes or chemistries. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A system for producing a sugar stream, the system comprising:
    a first grind device that is configured to receive and grind grain and/or grain components;
    a slurry tank that is situated after the first grind device and that is configured to receive a liquid and the ground grain and/or grain components, the liquid and ground grain and/or grain components defining a slurry including starch and unfermentable components;
    a liquefaction system that is situated after the slurry tank and that is configured to receive the slurry of the ground grain and/or grain components, which includes the starch and unfermentable components, and convert the starch in the slurry to oligosaccharides;
    a saccharification system that is situated after the liquefaction system and that is configured to receive the slurry including the oligosaccharides, and convert the oligosaccharides to simple sugars thereby producing a stream including the simple sugars and unfermentable components;
    a first separation device selected from a paddle screen, a vibration screen, a screen decanter centrifuge, a conic screen centrifuge, a pressure screen, a preconcentrator, or a filter press that is situated after the saccharification system and that is configured to receive and separate the stream into a solids portion including the unfermentable components and a liquid portion including the simple sugars;
    a sugar separation device selected from a clarifier or a filtration centrifuge that is situated after the first separation device and that is configured to receive the liquid portion and separate out heavier residual protein from the liquid portion, wherein the sugar separation device is capable of producing a liquid portion, after the heavier residual protein is separated out, having a dextrose equivalent of at least 70 D.E. and a total unfermentable solids fraction that is less than or equal to 30% of the total solids content; and
    a microfiltration device that is situated after the sugar separation device and that is configured to receive the liquid portion therefrom and filter out additional insoluble components from the liquid portion, wherein the microfiltration device is capable of producing a liquid portion, after microfiltration, which defines a sugar stream having a total unfermentable solids fraction that is less than or equal to 10% of the total solids content.

2. The system of claim 1 further comprising a biofuel and/or biochemical device that is situated after the microfiltration device and that is configured to receive the sugar stream and produce biofuel and/or biochemicals from the simple sugars.

3. The system of claim 1 further including a second grind device that follows the first grind device and that is configured to receive and further grind the slurry of ground grain and/or grain components.

4. The system of claim 1 wherein the sugar stream includes the simple sugars and free oil, and further comprising an oil separator that is situated after the first separation device and prior to the sugar separation device and that is configured to receive the liquid portion and separate the free oil from the liquid portion to yield an oil co-product.

5. The system of claim 4 wherein the oil separator is a mud centrifuge, a two or three phase decanter, a disc decanter, a two or three phase disc centrifuge, a flotation tank, or a dissolved air flotation tank.

6. The system of claim 4 further comprising an oil polish device that is situated after the oil separator and that is configured to receive and further purify the free oil from the oil separator to yield an oil co-product.

7. The system of claim 1 further comprising a second separation device that is situated after the first separation device and that is configured to receive and separate the solids portion into a second solids portion including unfermentable components and a second liquid portion including simple sugars.

8. The system of claim 7 further comprising a third separation device that is situated after the second separation device and that is configured to receive and separate the second solids portion into a thirds solids portion including unfermentable components and a third liquid portion including simple sugars.

9. system of claim 8 further comprising a fourth separation device that is situated after the third separation device and that is configured to receive and separate the third solids portion into a fourth solids portion, including fiber, and a fourth liquid portion.

10. The system of claim 1 wherein the unfermentable components of the solids portion includes fiber and protein, and further comprising a second separation device that is situated after the first separation device and that is configured to receive and separate the solids portion into a second solids portion, including the fiber, and a second liquid portion, including the protein, and a protein separation device that is situated after the second separation device and that is configured to receive the second liquid portion and separate out the protein from the second liquid portion to yield a protein co-product.

11. The system of claim 1 wherein the grain and/or grain component are one or more selected from the group consisting of corn, wheat, barley, sorghum, rye, rice, oats, sugar cane, tapioca, and cassava.

12. The system of claim 1 further comprising a second separation device that is situated after the first separation device and that is configured to receive and separate the solids portion into a second solids portion including unfermentable components and a second liquid portion including simple sugars, wherein the system is configured to combine the separated sugar stream from the first separation device and the separated sugar stream from the second separation device.

13. A system for producing a sugar stream, the system comprising:
- a first grind device that is configured to receive and grind grain and/or grain components;
- a slurry tank that is situated after the first grind device and that is configured to receive a liquid and the ground grain and/or grain components, the liquid and ground grain and/or grain components defining a slurry including starch and unfermentable components;
- a liquefaction system that is situated after the slurry tank and that is configured to receive the slurry of the ground grain and/or grain components, which includes the starch and unfermentable components, and convert the starch in the slurry to oligosaccharides;
- a saccharification system that is situated after the liquefaction system and that is configured to receive the slurry including the oligosaccharides, and convert the oligosaccharides to simple sugars thereby producing a stream including the simple sugars and unfermentable components;
- a first separation device selected from a paddle screen, a vibration screen, a screen decanter centrifuge, a conic screen centrifuge, a pressure screen, a preconcentrator, or a filter press that is situated after the saccharification system and that is configured to receive and separate the stream into a solids portion including the unfermentable components and a liquid portion including the simple sugars;
- a sugar separation device selected from a clarifier or a filtration centrifuge that is situated after the first separation device and that is configured to receive the liquid portion and separate out heavier residual protein from the liquid portion, wherein the sugar separation device is capable of producing a liquid portion, after the heavier residual protein is separated out, having a dextrose equivalent of at least 70 D.E. and a total unfermentable solids fraction that is less than or equal to 30% of the total solids content;
- a microfiltration device that is situated after the sugar separation device and that is configured to receive the liquid portion therefrom and filter out additional insoluble components from the liquid portion, wherein the microfiltration device is capable of producing a liquid portion, after microfiltration, which defines a sugar stream having a total unfermentable solids fraction that is less than or equal to 10% of the total solids content; and
- a reactor that is situated after the microfiltration device and that is configured to receive the sugar stream and produce biofuel from the simple sugars.

14. The system of claim 13 wherein the reactor is a fermenter that receives the sugar stream and produces an alcohol from the simple sugars.

15. The system of claim 13 further including a second grind device that follows the first grind device and that is configured to receive and further grind the slurry of ground grain and/or grain components.

16. The system of claim 13 wherein the sugar stream includes the simple sugars and free oil, and further comprising an oil separator that is situated after the first separation device and prior to the sugar separation device and that is configured to receive the liquid portion and separate the free oil from the liquid portion to yield an oil co-product.

17. The system of claim 16 wherein the oil separator is a mud centrifuge, a two or three phase decanter, a disc decanter, a two or three phase disc centrifuge, a flotation tank, or a dissolved air flotation tank.

18. The system of claim 16 further comprising an oil polish device that is situated after the oil separator and that is configured to receive and further purify the free oil from the oil separator to yield an oil co-product.

19. The system of claim 13 further comprising a second separation device that is situated after the first separation device and that is configured to receive and separate the solids portion into a second solids portion including unfermentable components and a second liquid portion including simple sugars.

20. The system of claim 19 further comprising a third separation device that is situated after the second separation device and that is configured to receive and separate the second solids portion into a thirds solids portion including unfermentable components and a third liquid portion including simple sugars.

21. The system of claim 20 further comprising a fourth separation device that is situated after the third separation device and that is configured to receive and separate the third solids portion into a fourth solids portion, including fiber, and a fourth liquid portion.

22. The system of claim 13 wherein the unfermentable components of the solids portion includes fiber and protein, and further comprising a second separation device that is situated after the first separation device and that is configured to receive and separate the solids portion into a second solids portion, including the fiber, and a second liquid portion, including the protein, and a protein separation device that is situated after the second separation device and that is configured to receive the second liquid portion and separate out the protein from the second liquid portion to yield a protein co-product.

23. The system of claim 13 wherein the grain and/or grain component are one or more selected from the group consisting of corn, wheat, barley, sorghum, rye, rice, oats, sugar cane, tapioca, and cassava.

24. The system of claim 13 further comprising a second separation device that is situated after the first separation device and that is configured to receive and separate the solids portion into a second solids portion including unfermentable components and a second liquid portion including simple sugars, wherein the system is configured to combine the separated sugar stream from the first separation device and the separated sugar stream from the second separation device.

* * * * *